(12) United States Patent
Gotoh

(10) Patent No.: US 7,246,943 B2
(45) Date of Patent: Jul. 24, 2007

(54) X-RAY DIAGNOSTIC APPARATUS

(75) Inventor: Atsushi Gotoh, Kuroiso (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 93 days.

(21) Appl. No.: 11/069,957

(22) Filed: Mar. 3, 2005

(65) Prior Publication Data
US 2005/0195945 A1    Sep. 8, 2005

(30) Foreign Application Priority Data
Mar. 5, 2004    (JP) .............................. 2004-062038

(51) Int. Cl.
*H05G 1/02* (2006.01)
(52) U.S. Cl. ...................... 378/196; 378/197
(58) Field of Classification Search ........ 378/193–198, 378/117
See application file for complete search history.

(56) References Cited

U.S. PATENT DOCUMENTS 4,884,293 A * 11/1989 Koyama ..................... 378/197
5,367,554 A * 11/1994 Kobayashi et al. ......... 378/196
6,325,537 B1 * 12/2001 Watanabe ................... 378/197
6,435,713 B1 * 8/2002 Iizuka ........................ 378/195
6,508,586 B2 * 1/2003 Oota .......................... 378/196

FOREIGN PATENT DOCUMENTS

JP    56-72848    6/1981
JP    62-66598    3/1987

\* cited by examiner

*Primary Examiner*—Jurie Yun
(74) *Attorney, Agent, or Firm*—Oblon, Spivak, McClelland, Maier & Neustadt, P.C.

(57) ABSTRACT

An X-ray diagnostic apparatus includes a first arm mounted with a first X-ray tube and a first X-ray detector, a second arm mounted with a second X-ray tube and a second X-ray detector, a bed having a table top capable of rising and falling on which a patient is placed, a first rotating mechanism that rotates the first arm, a first moving mechanism that subjects the first arm to parallel translation, and a control unit that controls the first rotating mechanism and the first moving mechanism on the basis of a position of the second arm.

14 Claims, 5 Drawing Sheets

X-RAY DIAGNOSTIC APPARATUS

CROSS-REFERENCE TO RELATED APPLICATIONS

This application is based upon and claims the benefit of priority from prior Japanese Patent Application No. 2004-062038, filed Mar. 5, 2004, the entire contents of which are incorporated herein by reference.

BACKGROUND OF THE INVENTION

1. Field of the Invention

The present invention relates to a biplane X-ray diagnostic apparatus that makes it possible to perform simultaneous imaging in two directions.

2. Description of the Related Art

A biplane X-ray diagnostic apparatus, which has been developed mainly for inspection of the circulatory system, includes two X-ray imaging systems, namely, a frontal X-ray imaging system for imaging a patient from the front thereof and a lateral X-ray imaging system for imaging the patient from the side thereof, in order to make it possible to image the patient from two directions simultaneously. The frontal X-ray imaging system has an X-ray tube and an X-ray detector that are attached to both ends of a C arm supported by, for example, a stand placed on a floor. Similarly, the lateral X-ray imaging system has an X-ray tube and an X-ray detector that are attached to both ends of an Ω arm suspended from a ceiling.

Since the C arm of the frontal X-ray imaging system has the stand fixed to the floor, the C arm is capable of turning (pivoting) around the stand but, basically, cannot move on the floor. On the other hand the Ω arm of the lateral X-ray imaging system is suspended from sliders engaged with rails provided on the ceiling to be movable longitudinal and lateral along the rails. In radioscopy and imaging, the C arm and the Ω arm are initially aligned such that a region of interest of a patient is located in image centers in both the frontal X-ray imaging system and the lateral X-ray imaging system. In other words, the C arm and the Ω arm are aligned such that the region of interest of the patient is located on an imaging center axis of the frontal X-ray imaging system and located on an imaging center axis of the lateral X-ray imaging system.

Even if the region of interest is positioned on the respective imaging center axis, the region of interest does not always coincide with a rotation center point of the C arm and a rotation center point of the Ω arm. In this case, when the C arm or the Ω arm is rotated, the region of interest deviates from the respective imaging center axes. Consequently, since the region of interest deviates from the image centers, it is necessary to perform positioning of the region of interest again.

BRIEF SUMMARY OF THE INVENTION

It is an object of the invention to always position a region of interest in image centers regardless of rotation of arms in a biplane X-ray diagnostic apparatus.

An X-ray diagnostic apparatus according to a first aspect of the invention includes: a first arm mounted with a first X-ray tube and a first X-ray detector; a second arm mounted with a second X-ray tube and a second X-ray detector; a bed having a table top capable of rising and falling on which a patient is placed; a first rotating mechanism that rotates the first arm; a first moving mechanism that subjects the first arm to parallel translation; and a control unit that controls the first rotating mechanism and the first moving mechanism on the basis of a position of the second arm.

An X-ray diagnostic apparatus according to a second aspect of the invention includes: a first arm mounted with a first X-ray tube and a first X-ray detector; a second arm mounted with a second X-ray tube and a second X-ray detector; a bed having a table top on which a patient is placed; a first rotating mechanism that rotates the first arm; a first moving mechanism that subjects the first arm to parallel translation; and a control unit that controls the first moving mechanism in order to subject the first arm to parallel translation following the rotation of the first arm.

An X-ray diagnostic apparatus according to a third aspect of the invention includes: an arm mounted with an X-ray tube and an X-ray detector; a bed having a table top on which a patient is placed; a rotating mechanism that rotates the arm; a moving mechanism that subject the arm to parallel translation; and a control unit that controls the moving mechanism to subject the arm to parallel translation following the rotation of the arm such that a specific region of the patient is located on an imaging axis.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
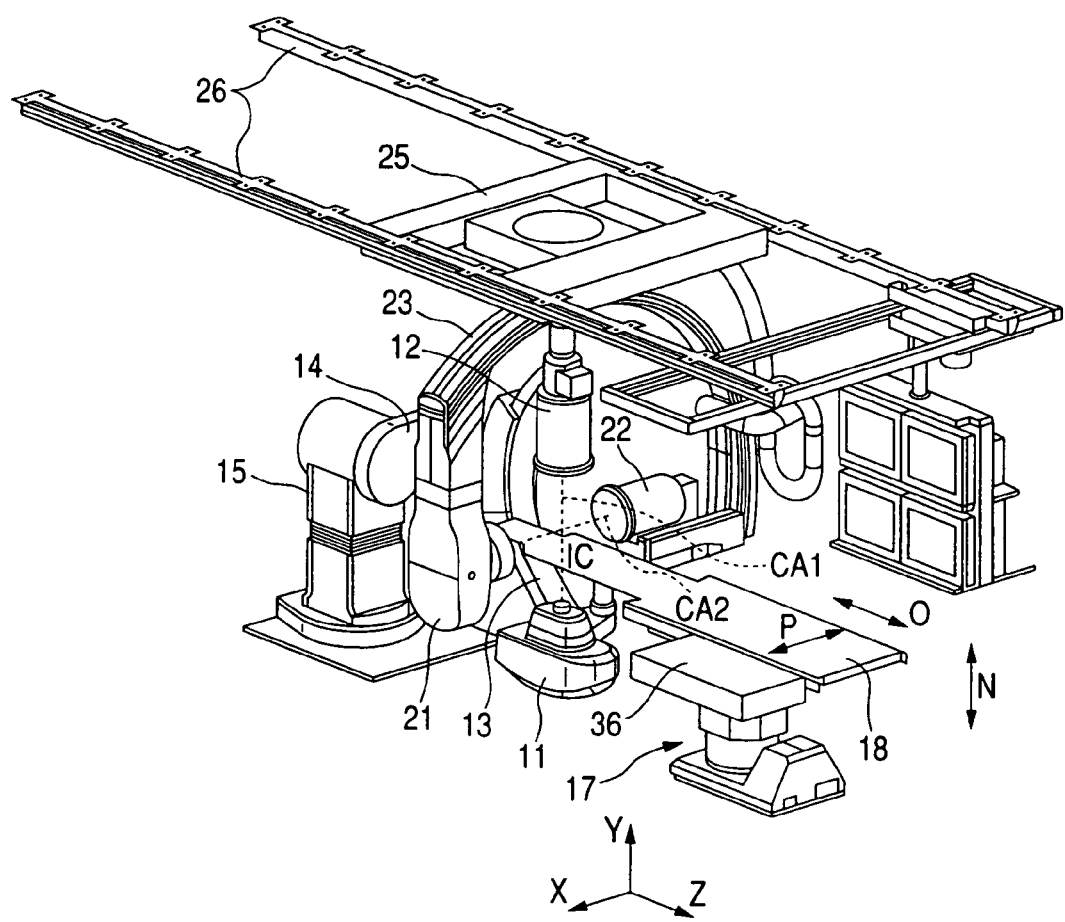
FIG. 1 is an external view of a biplane X-ray diagnostic apparatus according to an embodiment of the invention.
Figure 2:
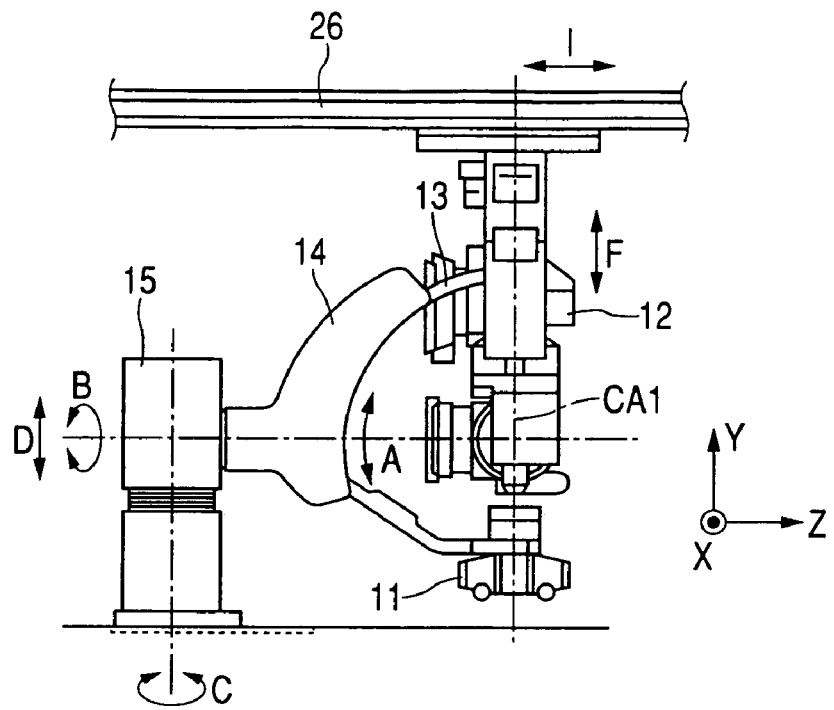
FIG. 2 is a side view of the biplane X-ray diagnostic apparatus in FIG. 1.
Figure 3:
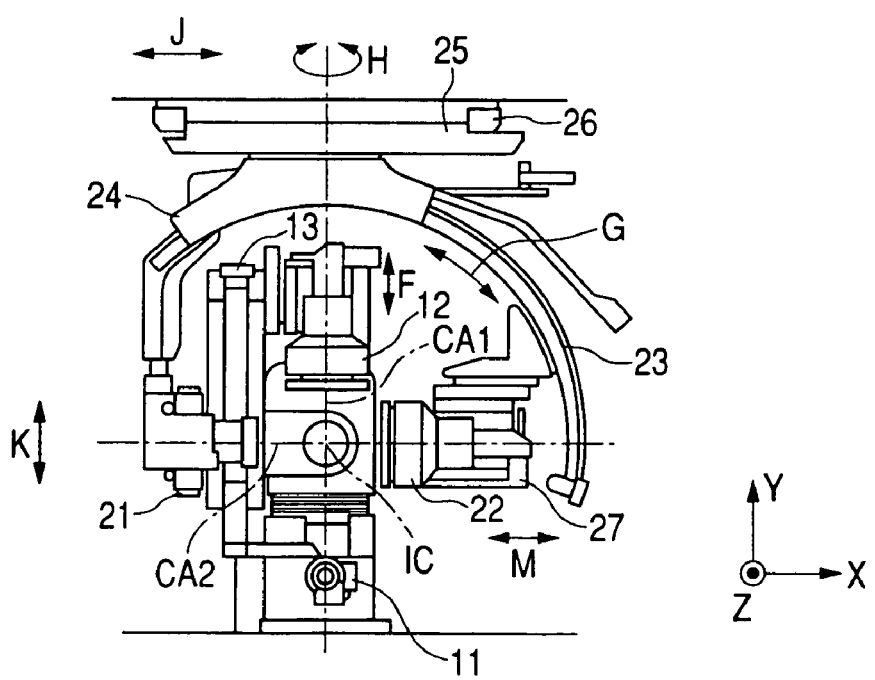
FIG. 3 is a frontal view of the biplane X-ray diagnostic apparatus in FIG. 1.

An X-ray diagnostic apparatus according to an embodiment of the invention will be hereinafter explained with reference to the accompanying drawings. FIG. 1 shows an external appearance of the X-ray diagnostic apparatus according to the embodiment. FIG. 2 is a side view of the X-ray diagnostic apparatus and FIG. 3 is a front view of the X-ray diagnostic apparatus. This X-ray diagnostic apparatus is applicable to a biplane system and includes a frontal X-ray imaging system (a first X-ray imaging system) and a lateral X-ray imaging system (a second X-ray imaging system) to be capable of imaging a patient placed on a table top 18 of a bed 17 from two directions simultaneously.

The frontal X-ray imaging system has an X-ray tube (a first X-ray tube) 11 and an X-ray detector (a first X-ray detector) 12. The lateral X-ray imaging system has an X-ray tube (a second X-ray tube) 21 and an X-ray detector (a second X-ray detector) 22. As the X-ray detectors 12 and 22, a combination of an image intensifier and a TV camera or a flat panel detector (FPD) is adopted.

The X-ray tube 11 is attached to one end of a C arm 13. The X-ray detector 12 is attached to the other end of the C arm 13 so as to be approachably and separably with respect to a rotation center point RC1 (in a direction of an arrow F). Reference sign CA1 denotes an imaging center axis of the frontal X-ray imaging system connecting a focal point of the X-ray tube 11 and a center of an image reception area of the X-ray detector 12. The X-ray tube 12 is attached to one end of an Ω arm 23. The X-ray detector 22 is attached to the other end of the Ω arm 23 so as to be approachably and separably with respect to a rotation center point RC2 (in a direction of an arrow M). Reference sign CA2 denotes an imaging center point of the lateral X-ray imaging system connecting a focal point of the X-ray tube 21 and a center of an image reception area of the X-ray detector 22.

The C arm 13 of the frontal X-ray imaging system is supported by a stand 15 fixed on a floor via an arm holder 14. The arm holder 14 holds the C arm 13 to be slidingly rotatable in a direction of an arrow A. The stand 15 holds the arm holder 14 to be axially rotatable in a direction of an arrow B. The stand 15 is capable of pivoting (turning) in a direction of an arrow C. The stand 15 holds the arm holder 14 to be movable in a vertical direction (capable of rising and falling) in a direction of an arrow D. With such a structure, it is possible to incline an imaging angle of the frontal X-ray photographing system arbitrarily in the directions of the arrows A and B. An intersection of a rotation axis of the arrow A and a rotation axis of the arrow B is referred to as a rotation center point RC1. It is possible to retract the frontal X-ray imaging system and the C arm 13 from an imaging position by causing the stand 15 to turn in the direction of the arrow C. In addition, it is possible to move the C arm 13 to an arbitrary height by causing the stand 15 to rise and fall in the direction of the arrow D. In addition, the above-mentioned enforcement form is applicable also to a system without the arrow D.

The Ω arm 23 of the lateral X-ray imaging system is suspended from a slider base 25 via an arm holder 24. The arm holder 24 holds the Ω arm 23 to be slidingly rotatable in a direction of an arrow G. The slider base 25 holds the arm holder 24 to be axially rotatable in a direction of an arrow H. The Ω arm 23 holds the X-ray tube 21 and the X-ray detector 22 to be capable of rising and falling in a direction of an arrow K. An intersection of a rotation axis of the arrow G and a rotation axis of the arrow H is referred to as a rotation center point RC2. The slider base 25 is engaged with a traveling rail 26 provided on a ceiling surface to be movable longitudinal and lateral in directions of arrows I and J.

The bed 17 supports the table top 18 to be capable of rising and falling in a vertical direction N and to be slidable in a direction O parallel to a long axis direction Z thereof and a direction P parallel to a lateral axis direction X thereof.

Figure 4:
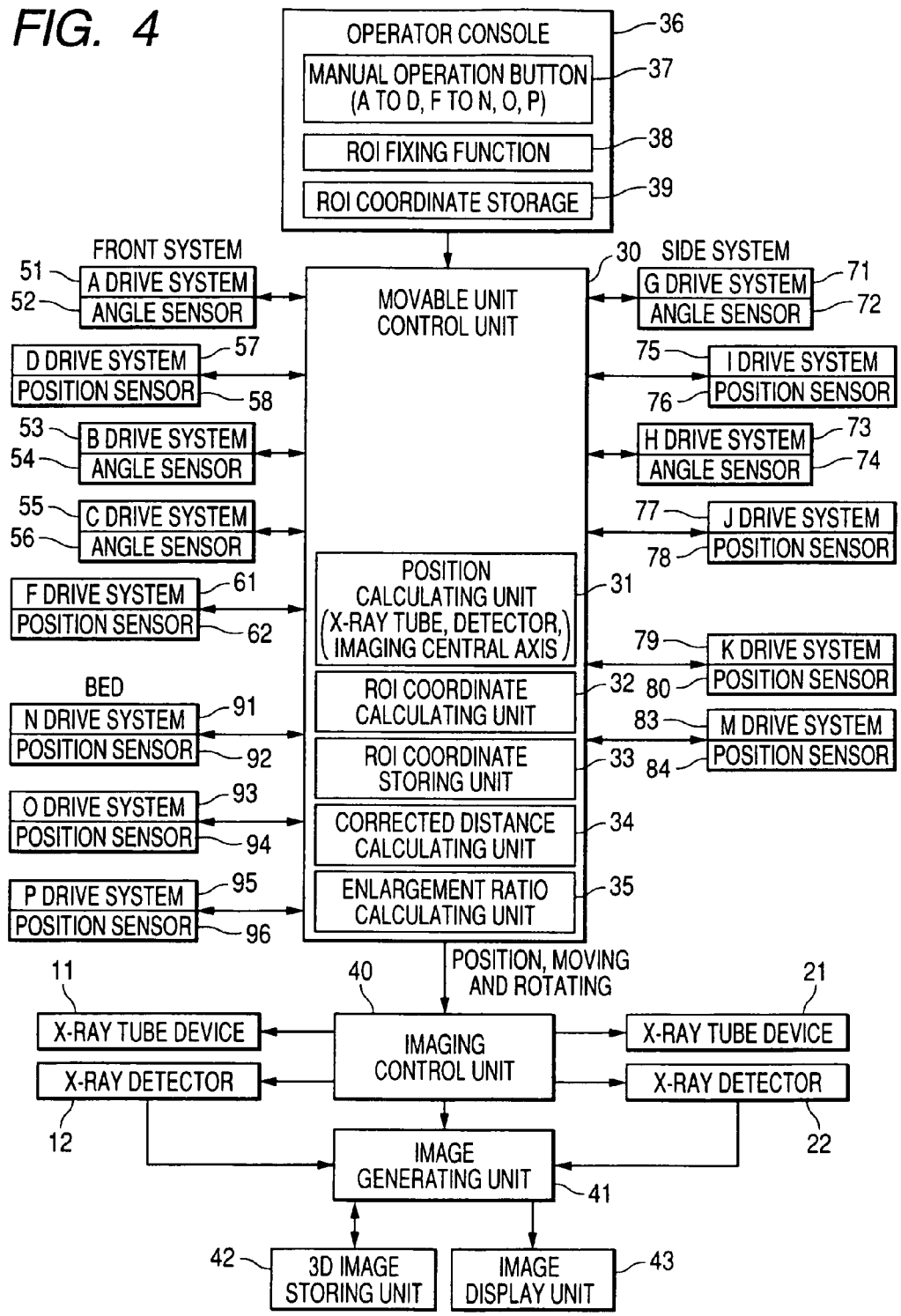
FIG. 4 is a movable section control system diagram of an X-ray diagnostic apparatus in FIG. 1.

The movements in the directions A to D, F to N, and O and P of the movable sections can be operated individually by manual operation buttons 37 on an operator's console 36 that is set near the bed 17 (see FIG. 4). The manual operation buttons 37 correspond to the movable sections that move in the directions A to O. The operator's console 36 includes an ROI fixing function button 38 that switches ON and OFF of an automatic control function (an ROI fixing function) for fixing the region of interest ROI in an image center and an ROI coordinate storage button 39 for storing coordinates of the region of interest in addition to the manual operation buttons 37. A movable section control unit 30 is connected to the operator's console 36.

Concerning the frontal X-ray imaging system, drive systems 51, 53, 55, 57, and 61, which correspond to the respective movements in the directions A, B, C, D, and F, are connected to the movable section control unit 30 together with sensors 52, 54, 56, 58, and 62 therefor. Similarly, concerning the lateral X-ray imaging system, drive systems 71, 73, 75, 77, 79, and 83, which correspond to the respective movements in the directions G, H, I, J, K, and M, are connected to the movable section control unit 30 together with sensors 72, 74, 76, 78, 80, and 84 therefor. Concerning the bed, drive systems 91, 93, and 95, which correspond to the respective movements in the directions N, O, and P, are connected to the movable section control unit 30 together with sensors 92, 94, and 96 therefor. In accordance with an instruction of an operator inputted via the manual operation buttons 37 of the operator's console 36, the movable section control unit 30 outputs a drive signal to a drive system corresponding to a movable section to which the instruction is sent and inputs a sensor output signal. In the case of manual operation, the movable section control unit 30 outputs a brake or clutch release signal.

In addition to the manual operation control function, in order to realize an ROI fixing function for fixing a region of interest in an image center, the movable section control unit 30 includes a position calculating unit 31, an ROI coordinate calculating unit 32, an ROI coordinate storing unit 33, a corrected distance calculating unit 34, and a magnification ratio calculating unit 35. The position calculating unit 31 calculates coordinates of a position of a focal point of the X-ray tube 11 on the basis of outputs of the sensors 52, 54, 56, and 58 that detect angles and positions of the movable sections, which move in the directions A, B, C, and D, of the frontal X-ray imaging system. Similarly, the position calculating unit 31 calculates coordinates of a position of a center point of the X-ray detector 12 on the basis of outputs of the sensors 52, 54, 56, 58, and 62 that detect angles and positions of the movable sections, which move in the directions A, B, C, D, and F, of the frontal X-ray imaging system. Moreover, the position calculating unit 31 obtains a linear equation of the imaging center axis CA1 connecting the calculated focal point of the X-ray tube 11 and the calculated center point of the X-ray detector 12.

Similarly, concerning the lateral X-ray imaging system, the position calculating unit 31 calculates coordinates of a position of a focal point of the X-ray tube 21 on the basis of outputs of the sensors 72, 74, 76, 78, and 80 that detect angles and positions of the movable sections, which move in the directions G, H, I, J, and K, of the lateral X-ray imaging system. The position calculating unit 31 also calculates coordinates of a position of a center point of the X-ray detector 22 on the basis of outputs of the sensors 72, 74, 76, 78, 80, and 84 that detect angles and positions of the movable sections, which move in the directions G, H, I, J, K, and M, of the lateral X-ray imaging system. The position calculating unit 31 obtains a linear equation of the imaging center axis CA2 connecting the calculated focal point of the X-ray tube 21 and the calculated center point of the X-ray detector 22.

Figure 5:
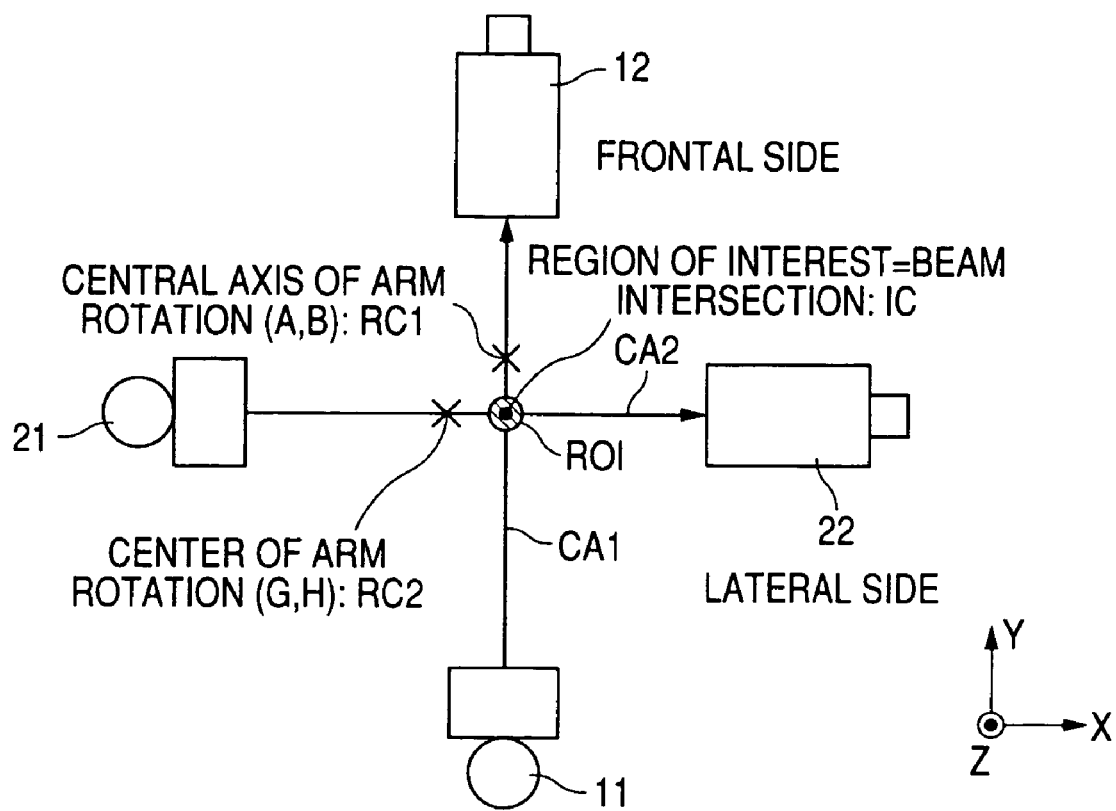
FIG. 5 is a diagram showing a positional relation between a beam center axis and a region of interest (ROI) at a point when coordinates of the region of interest are stored in the embodiment.

The ROI coordinate calculating unit 32 calculates coordinates of an intersection of the imaging center axis CA1 and the imaging center axis CA2 at a point when the ROI coordinate storage button 39 is pressed by an operator as ROI coordinate. The operator operates the arms 13 and 23 and the table top 18 manually to press the ROI coordinate storage button 39 in a state in which a region of interest substantially coincides with a center of an image formed by the frontal X-ray imaging system and also substantially coincides with a center of an image formed by the lateral X-ray imaging system. In this state, a position of the region of interest coincides with the intersection IC of the imaging center axis CA1 and the imaging center axis CA2 (see FIG. 5). The calculated ROI coordinates are stored in the ROI coordinate storage unit 33. Note that, although the ROI coordinate storage button 39 is pressed in the example described above, instead of this, it is also possible that an automatic storage mode is provided to cause the ROI coordinate calculating unit 32 to automatically calculate and store ROI coordinates, for example, with first imaging as a trigger.

Figure 6:
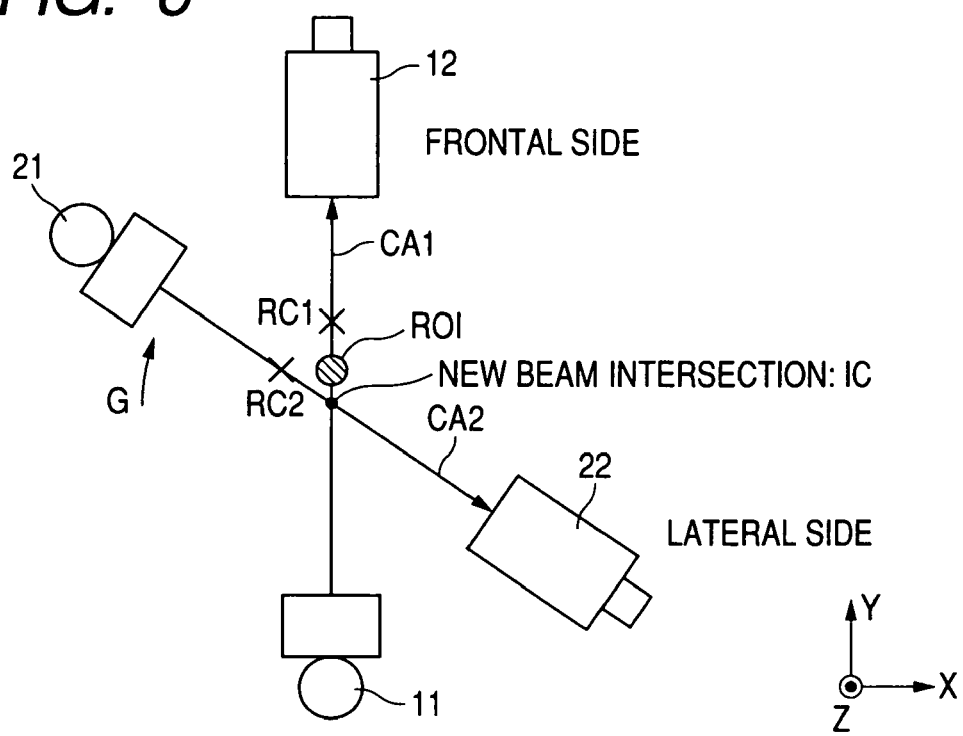
FIG. 6 is a diagram showing a positional deviation of the beam center axis with respect to the region of interest following rotation of an arm in the invention.
Figure 7:
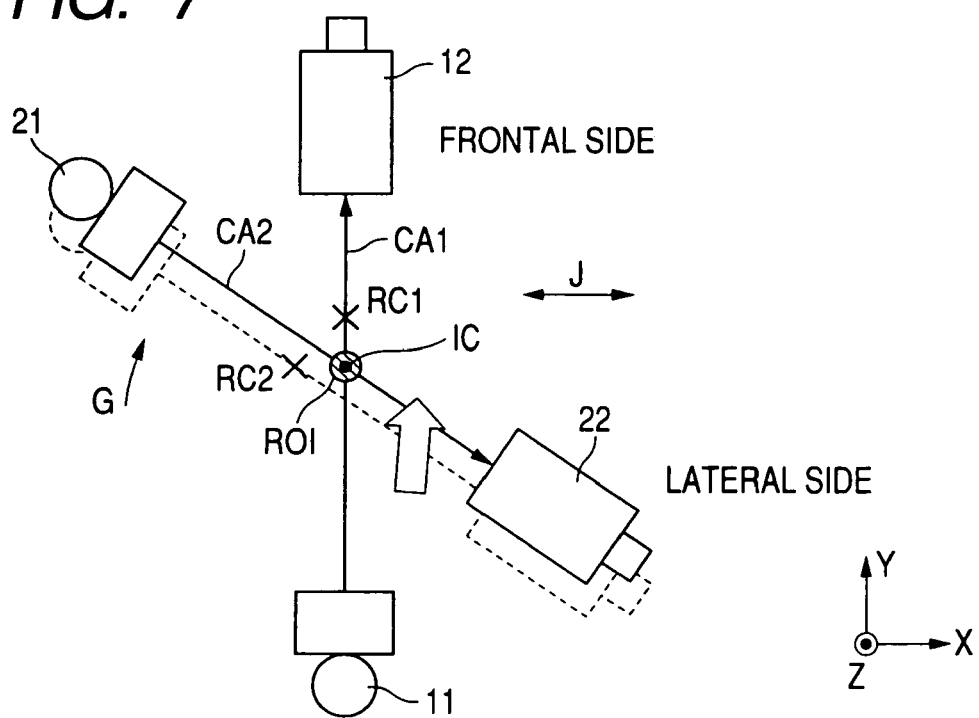
FIG. 7 is a diagram showing a corrected direction and a corrected distance for eliminating the positional deviation in FIG. 6.

In many cases, the intersection IC coincides with the region of interest but deviates from the rotation center points RC1 and RC2. Therefore, when the arms 13 and 23 are rotated (in the directions A, B, G, and H) from the initial state, as shown in FIG. 6, the intersection IC of the imaging center axis CA1 and the imaging center axis CA2 deviates from the region of interest. As a result, the region of interest deviates from the image center. The corrected distance calculating unit 34 for calculating moving directions and distances of the C arm 13 and the Ω arm 23 are provided such that, even if the C arm 13 and the Ω arm 23 are rotated form the initial state, the intersection IC of the imaging center axes CA1 and CA2 is substantially fixed in the region of interest following the rotation as shown in FIG. 7. Note that, the table top 18 may be moved instead of the movement of the C arm 13 and the Ω arm 23 or together with the movements of the C arm 13 and the Ω arm 23 such that the region of interest substantially coincides with the intersection IC of the imaging center axes CA1 and CA2.

For example, when the Ω arm 23 of the lateral X-ray imaging system is slidingly rotated in the direction G from the initial state by operation of the manual operation buttons 37 as shown in FIG. 6, the corrected distance calculating unit 34 calculates a moving direction (a rising and falling direction) K of the Ω arm 23 for correcting the deviation of the image center due to the rotation in the direction G and a moving distance thereof. The moving direction of the Ω arm 23 is a direction parallel to the imaging center axis CA1 of the C arm 13 and is, typically, the vertical direction. The corrected distance is calculated as a distance between the stored coordinate point of the region of interest (the intersection IC of the imaging center axes CA1 and CA2) and an intersection of the rotated imaging center axis CA2 and the imaging center axis CA1. In addition, the corrected distance is calculated on the basis of a rotation angle of the imaging center axis CA2. A rising and falling direction N and a corrected distance of the table top 18 may be calculated instead of calculating the moving direction (the rising and falling direction) K and the corrected distance of the Ω arm 23.

The Ω arm 23 is subjected to parallel translation by the calculated moving distance along the calculated moving direction K. The moving direction K and the moving distance of the Ω arm 23 are calculated repeatedly and the Ω arm 23 is subjected to parallel translation repeatedly every time the Ω arm 23 rotates a predetermined angle, for example, rotates once. Consequently, the Ω arm 23 is subjected to parallel translation following the rotation of the Ω arm 23. Even if the Ω arm 23 is rotated arbitrarily, the region of interest is always fixed in the image center.

Similarly, a moving direction K and a moving distance of the C arm 13 are calculated such that the intersection of the imaging center axis CA2 and the imaging center axis CA1 is fixed to the region of interest when the C arm 13 is rotated. The C arm 13 is subjected to parallel translation in accordance with the calculated moving direction K and the calculated moving distance. The moving direction K and the moving distance of the C arm 13 are calculated repeatedly and the C arm 13 is subjected to parallel translation repeatedly every time the C arm 13 rotates a predetermined angle, for example, rotates once. Consequently, the C arm 13 is subjected to parallel translation following the rotation of the C arm 13. Even if the C arm 13 is rotated arbitrarily, the region of interest is always fixed in the image center.

In this way, even if the region of interest deviates from the rotation center points RC1 and RC2 of the arms 13 and 23, it is possible to always locate the region of interest in the respective image centers by moving the arms 13 and 23 in directions corresponding to rotations thereof and by distances corresponding to rotation angles thereof following the rotations.

Here, an imaging magnification ratio is given as a ratio of a distance from the focal points of the X-ray tubes 11 and 21 to the X-ray detectors 12 and 22 with respect to a distance from the focal points of the X-ray tubes 11 and 21 to the region of interest. In a state in which the region of interest deviates from the rotation center points RC1 and RC2 of the arms 13 and 23, the arms 13 and 23 are rotated around the rotation center points RC1 and RC2 and positional deviation following the rotations of the arms 13 and 23 is eliminated by parallel translation of the arms 13 and 23. Thus, the imaging magnification ratio changes from that in the initial state. The magnification ratio calculating unit 35 calculates an imaging magnification ratio in the initial state of the frontal X-ray imaging system from the position in the initial state of the X-ray tube 11, the position of the region of interest (the intersection IC), and the position in the initial state of the X-ray detector 12 and holds the imaging magnification ratio.

The magnification ratio calculating unit 35 calculates an imaging magnification ratio after correction movement of the frontal X-ray imaging system from a position of the X-ray tube 11 after rotation and correction movement of the C arm 13, the position of the region of interest (the intersection IC), and the position in the initial state of the X-ray detector 12. The magnification ratio calculating unit 35 calculates a moving direction and a distance of the arm stand 15 with respect to the direction of the arrow D or F that are necessary for making the imaging magnification ratio after correction movement of the frontal X-ray imaging system identical with the imaging magnification ratio in the initial state. By moving the arm stand 15 in accordance with the calculated moving direction and distance, it is possible to maintain the imaging magnification ratio after the rotation of the C arm 13 at the imaging magnification ratio in the initial state. In addition, by maintaining the imaging magnification ratio, it is possible to realize an advantage that the X-ray tube 11 and the X-ray detector 12 are prevented from approaching the patient excessively.

Similarly, in the lateral X-ray imaging system, the magnification ratio calculating unit 35 calculates an imaging magnification ratio after correction movement of the lateral X-ray imaging system from a position of the X-ray tube 21 after rotation and correction movement of the Ω arm 23, the position of the region of interest (the intersection IC), the position in the initial state of the X-ray detector 22. The magnification ratio calculating unit 35 calculates moving directions and distances of the X-ray tube 21 and the X-ray detector 22 with respect to the direction of the arrow M and a moving direction and a distance of the slider base 25 with respect to the direction of the arrow I or J that are necessary for making the imaging magnification ratio after the correction movement of the lateral X-ray imaging system identical with the imaging magnification ratio in the initial state. By moving the X-ray tube 21, the X-ray detector 22, and the slider base 25 in accordance with the calculated moving directions and distances, respectively, it is possible to maintain an imaging magnification ratio after the rotation of the Ω arm 23 at the imaging magnification ratio in the initial state. In addition, by maintaining the imaging magnification ratio, it is possible to realize an advantage that the X-ray tube 21 and the X-ray detector 22 are prevented from approaching the patient excessively.

An imaging control unit 40 controls generation of an X-ray from the X-ray tube 11 and generation of an X-ray from the X-ray tube 21 to thereby control irradiation of the X-rays on a patient. It is possible to control the generation of the X-rays by applying a high voltage to the X-ray tube 11 from a high voltage control unit of the frontal X-ray imaging system and applying a high voltage to the X-ray tube 21 from a high voltage control unit of the lateral X-ray imaging system. The imaging control unit 40 controls collection of signals from the X-ray detectors 12 and 22 in synchronization with the irradiation of the X-rays on the patient.

Position data of the X-ray tube 11 of the frontal X-ray imaging system, position data of the X-ray detector 12 of the frontal X-ray imaging system, position data of the X-ray tube 21 of the lateral X-ray imaging system, and position data of the X-ray detector 22 of the lateral X-ray imaging system are instantaneously supplied to the imaging control unit 40 from the movable section control unit 30 together with data of the position of the region of interest (the position of the intersection IC in the initial state). In addition, a signal for identifying whether the C arm 13 is moving or stopped and a signal for identifying whether the Ω arm 23 is moving or stopped are supplied to the imaging control unit 40 from the movable section control unit 30 together with the position data.

Usually, when X-ray radioscopy and imaging are performed at a certain angle, radioscopy for obtaining a desired angle is often performed. This radioscopy causes useless radiation exposure that is not directly related to diagnosis and treatment. An image generating unit 41 is provided to solve the problem.

In a period instructed by the operator or at appropriate time, instead of the X-ray radioscopy and photographing involving X-ray irradiation, the image generating unit 41 performs dummy imaging without irradiation of an X-ray. In other words, the image generating unit 41 calculates an imaging direction and a magnification ratio of the frontal X-ray imaging system with respect to the region of interest on the basis of the data of the region of interest (the position of the intersection IC in the initial state), the position data of the X-ray tube 11 of the frontal X-ray imaging system, and the position data of the X-ray detector 12 of the frontal X-ray imaging system and subjects three-dimensional image data (also referred to as volume data) concerning the patient acquired by the X-ray diagnostic apparatus or other image diagnostic apparatuses like an X-ray CT apparatus in advance, which is stored in a 3D image storing unit 42, to projection processing in accordance with the calculated imaging direction and magnification ratio to thereby generate projected image data (dummy image data) that is substantially equivalent to an image obtained by actually generating an X-ray from the X-ray tube 11 and imaging the patient with the X-ray detector 12. Similarly, concerning the lateral X-ray imaging system, the image generating unit 41 calculates an imaging direction and a magnification ratio of the lateral X-ray imaging system with respect to the region of interest on the basis of the data of the region of interest, the position data of the X-ray tube 21 of the lateral X-ray imaging system, and the position data of the X-ray detector 22 of the lateral X-ray imaging system and subjects the three-dimensional image data stored in the 3D image storing unit 42 to projection processing in accordance with the calculated imaging direction and magnification ratio to thereby generate projected image data (dummy image data) that is substantially equivalent to an image obtained by actually generating an X-ray from the X-ray tube 21 and imaging the patient with the X-ray detector 22. Note that two-dimensional image data may be used instead of the three-dimensional image data.

Projected image data of the frontal X-ray imaging system, which is generated from the three-dimensional image data, is sent to an image display unit 43 together with projected image data of the lateral X-ray imaging system, which is generated from the same three-dimensional image data, and displayed on the image display unit 43.

As described above, in this embodiment, even if the arms 13 and 23 are rotated, it is possible to always maintain the region of interest of the patient in the image center. In addition, even if the arms 13 and 23 are rotating or moving, since projected images corresponding to photographing directions and magnification ratios at every moment are generated and displayed, it is possible to find angles suitable for the arms 13 and 23 under a guidance of images.

Note that, although the biplane X-ray diagnostic apparatus is described in the above explanation, the same explanation is applied to a single plane X-ray diagnostic apparatus as well.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray diagnostic apparatus comprising:
   a first arm mounted with a first X-ray tube and a first X-ray detector;
   a second arm mounted with a second X-ray tube and a second X-ray detector;
   a bed having a table top capable of rising and falling on which a patient is placed;
   a first rotating mechanism that rotates the first arm;
   a first moving mechanism that subjects the first arm to parallel translation;
   a control unit that controls the first rotating mechanism and the first moving mechanism on the basis of a position of the second arm; and wherein the control unit controls the first rotating mechanism and the first moving mechanism in order to substantially fix a position of an intersection of an imaging axis of the first arm and an imaging axis of the second arm.

2. An X-ray diagnostic apparatus according to claim 1, wherein the control unit controls the first moving mechanism in order to subject the first arm to parallel translation substantially in parallel to an imaging axis of the second arm.

3. An X-ray diagnostic apparatus according to claim 1, wherein the control unit subjects the first arm to parallel translation following the rotation of the first arm.

4. An X-ray diagnostic apparatus according to claim 1, wherein the control unit rotates the first arm following the movement of the first arm.

5. An X-ray diagnostic apparatus according to claim 1, wherein the control unit causes the table top to rise and fall following the movement of the first arm.

6. An X-ray diagnostic apparatus according to claim 1, further comprising:
   a second rotating mechanism that rotates the second arm; and
   a second moving mechanism that subjects the second arm to parallel translation.

7. An X-ray diagnostic apparatus according to claim 6, wherein the control unit controls the second rotating mechanism and the second moving mechanism on the basis of a position of the first arm.

8. An X-ray diagnostic apparatus according to claim 1, further comprising:
   a storing unit that stores three-dimensional data concerning the patient;
   an image generating unit that generates first projected image data, which corresponds to a position and a direction of the first arm, and second projected image data, which corresponds to a position and a direction of the second arm, from the stored three-dimensional image data during a period of movement of at least one of the first arm, the second arm, and the table top; and
   a display unit that displays the generated first and second projected image data.

9. An X-ray diagnostic apparatus according to claim 1, wherein the control unit subjects the first arm to parallel translation along an imaging axis thereof in accordance with the rotation of the first arm in order to maintain an image magnification ratio to be substantially constant.

10. An X-ray diagnostic apparatus according to claim 1, wherein the control unit stops irradiation of an X-ray from the first and second X-ray tubes to the patient during a period of movement of at least one of the first arm, the second arm, and the table top.

11. An X-ray diagnostic apparatus comprising:
    a first arm mounted with a first X-ray tube and a first X-ray detector;
    a second arm mounted with a second X-ray tube and a second X-ray detector;
    a bed having a table top on which a patient is placed;
    a first rotating mechanism that rotates the first arm;
    a first moving mechanism that subjects the first arm to parallel translation;
    a control unit that controls the first moving mechanism in order to subject the first arm to parallel translation following the rotation of the first arm; and
    wherein the control unit controls the first moving mechanism in order to substantially fix a position of an intersection of an imaging axis of the first arm and an imaging axis of the second arm.

12. An X-ray diagnostic apparatus according to claim 11, wherein the control unit controls the first moving mechanism in order to move the first arm substantially in parallel to an imaging axis of the second arm.

13. An X-ray diagnostic apparatus according to claim 12, wherein the control unit causes the table top to rise and fall following the rotation of the first arm.

14. An X-ray diagnostic apparatus according to claim 11, further comprising:
    a second rotating mechanism that rotates the second arm; and
    a second moving mechanism that subjects the second arm to parallel translation, wherein
    the control unit controls the second moving mechanism in order to subject the second arm to parallel translation following the rotation of the second arm.

* * * * *